(12) United States Patent
Crockford

(10) Patent No.: US 11,698,384 B2
(45) Date of Patent: Jul. 11, 2023

(54) SYSTEM AND METHOD FOR MONITORING BODY MOVEMENT

(71) Applicant: Digital & Future Technologies Limited, Colchester (GB)

(72) Inventor: Christopher John Crockford, Colchester (GB)

(73) Assignee: DIGITAL & FUTURE TECHNOLOGIES LIMITED, Colchester (GB)

(*) Notice: Subject to any disclaimer, the term of this patent is extended or adjusted under 35 U.S.C. 154(b) by 206 days.

(21) Appl. No.: 17/126,896

(22) Filed: Dec. 18, 2020

(65) Prior Publication Data

US 2021/0190811 A1 Jun. 24, 2021

(30) Foreign Application Priority Data

Dec. 20, 2019 (GB) ..................... 1919055

(51) Int. Cl.
*G01P 13/00* (2006.01)
*G01L 1/22* (2006.01)
*A61B 5/00* (2006.01)
*A61B 5/11* (2006.01)
*A61F 13/84* (2006.01)

(52) U.S. Cl.
CPC ............ *G01P 13/00* (2013.01); *A61B 5/1126* (2013.01); *A61B 5/4528* (2013.01); *A61B 5/746* (2013.01); *A61F 13/84* (2013.01); *G01L 1/225* (2013.01); *A61B 2562/0219* (2013.01); *A61B 2562/0261* (2013.01); *A61B 2562/063* (2013.01); *A61F 2013/8491* (2013.01)

(58) Field of Classification Search
None
See application file for complete search history.

(56) References Cited

U.S. PATENT DOCUMENTS

| | | | | |
|---|---|---|---|---|
| 6,540,707 | B1* | 4/2003 | Stark | A61F 5/02 602/19 |
| 11,246,213 | B2* | 2/2022 | Longinotti-Buitoni | D06P 1/5285 |
| 2009/0024062 | A1* | 1/2009 | Einarsson | A61B 5/486 600/595 |

(Continued)

FOREIGN PATENT DOCUMENTS

| | | |
|---|---|---|
| RU | 2537050 C1 | 12/2014 |
| WO | 2011/008934 A2 | 1/2011 |
| WO | 2016/044251 A1 | 3/2016 |

OTHER PUBLICATIONS

Tognetti A, Lorussi F, Mura GD, Carbonaro N, Pacelli M, Paradiso R, Rossi DD. New generation of wearable goniometers for motion capture systems. J Neuroeng Rehabil. Apr. 11, 2014;11:56. doi: 10.1186/1743-0003-11-56. PMID: 24725669; PMCID: PMC3996949. (Year: 2014).*

*Primary Examiner* — Benjamin S Melhus
(74) *Attorney, Agent, or Firm* — Occhiuti & Rohlicek LLP

(57) ABSTRACT

A method for determining the flexion or extension of a joint of a human or animal subject, comprising: applying a plurality of strain gauges to the joint in a known configuration; applying a first inertial measurement unit, IMU, to each strain gauge; receiving strain data from each of the strain gauges; receiving motion data from each of the IMUs; and calculating the flexion or extension of the joint in dependence on the received strain data, motion data and the configuration of the strain gauges.

17 Claims, 2 Drawing Sheets

(56) References Cited

U.S. PATENT DOCUMENTS

| | | | |
|---|---|---|---|
| 2009/0024065 A1* | 1/2009 | Einarsson | A61B 5/4528 600/587 |
| 2011/0213275 A1* | 9/2011 | Boos | A61B 5/1121 600/595 |
| 2011/0257928 A1* | 10/2011 | Cunningham | G01L 1/00 324/109 |
| 2012/0238914 A1* | 9/2012 | Goldfield | A61B 5/6828 600/595 |
| 2014/0070957 A1* | 3/2014 | Longinotti-Buitoni | A61B 5/02055 340/870.01 |
| 2014/0318699 A1* | 10/2014 | Longinotti-Buitoni | H05K 1/038 156/247 |
| 2015/0040282 A1* | 2/2015 | Longinotti-Buitoni | A61B 5/742 2/69 |
| 2015/0051515 A1* | 2/2015 | Cunningham | G01L 25/006 600/595 |
| 2015/0309563 A1* | 10/2015 | Connor | A61B 5/1071 73/865.4 |
| 2015/0366504 A1 | 12/2015 | Connor | |
| 2016/0202755 A1* | 7/2016 | Connor | G06F 3/011 73/865.4 |
| 2016/0302721 A1* | 10/2016 | Wiedenhoefer | A61B 5/1126 |
| 2016/0310140 A1* | 10/2016 | Belson | A61B 17/08 |
| 2017/0086671 A1* | 3/2017 | Sessler | G16H 40/67 |
| 2017/0156664 A1* | 6/2017 | Belson | A61M 31/002 |
| 2017/0348155 A1 | 12/2017 | Duesterhoft et al. | |
| 2018/0184735 A1* | 7/2018 | Longinotti-Buitoni | A63B 24/0062 |
| 2019/0117156 A1* | 4/2019 | Howard | A61B 5/6824 |
| 2019/0224841 A1* | 7/2019 | Ly | A61B 5/4504 |
| 2019/0328330 A1* | 10/2019 | Inan | A61B 5/6844 |
| 2020/0093383 A1* | 3/2020 | Arkans | A61B 5/4836 |
| 2021/0236025 A1* | 8/2021 | Comtois | A61B 5/6804 |

\* cited by examiner

SYSTEM AND METHOD FOR MONITORING BODY MOVEMENT

CROSS-REFERENCE TO RELATED APPLICATIONS

Priority is claimed to British Patent Application No. 1919055.2, filed Dec. 20, 2019, the content of which is incorporated herein by reference

FIELD

This invention relates to monitoring apparatus and methods, particularly medical dressings comprising sensing apparatus.

BACKGROUND

It is often desirable for physical properties to be measured on or around the human body. The fields of medicine and personal fitness are two areas where this is particularly common. Monitoring the activity of a wounded person is advantageous for the care the and management of the wound and for the long-term rehabilitation. Detailed knowledge of the mobility of a person and of the forces exerted on the body during can enable doctors or physiotherapists to better assess extent of injuries and the better provide for the care of patients.

Conventional monitoring methods have struggled to provide accurate, reliable methods of monitoring movement of the body, particularly at the joints. Conventional monitoring systems have also lacked portability or, when portable, have lacked longevity due to their severely restricted battery life.

There is a need for an improved mechanism for monitoring the movement of a human or animal body.

SUMMARY OF THE INVENTION

According to the present invention there is provided a method for determining the flexion or extension of a joint of a human or animal subject, comprising: applying a plurality of strain gauges to the joint in a known configuration; receiving strain data from each of the strain gauges; and calculating the flexion or extension of the joint in dependence on the received data and the configuration of the strain gauges.

The method may further comprise applying a first inertial measurement unit, IMU, to each strain gauge, receiving motion data from each of the IMUs, and wherein the flexion or extension is calculated in dependence on the motion data. The method may further comprise applying a second IMU to each strain gauge, the first and second IMUs being applied to opposing ends of their respective strain gauges.

The motion data received from the IMUs may be adjusted in dependence on the data received from strain gauges.

The motion data received from the IMUs may be disregarded or down-weighted in the calculation of the flexion or extension in dependence on the received data.

The received strain data may be adjusted in dependence on the motion data received from the IMUs.

The received strain data may be disregarded or down-weighted in the calculation of the flexion or extension in dependence on the motion data received from the IMUs.

The known configuration may comprise a stacked configuration. The known configuration may comprise two strain gauges being arranged on opposing sides of the joint.

There is also provided a medical dressing comprising: a strain gauge configured to measure the strain applied to the dressing surface; an interface configured to enable data from the strain gauge to be offloaded to an external system; and a power management unit configured to, in response to the strain gauge detecting a first predefined strain pattern, cause the interface to enter a reduced power mode in which the offload of data is reduced.

Detecting the first predefined strain pattern may comprise detecting that the measured strain has dropped below a predetermined strain threshold.

Detecting the first predefined strain pattern may comprise detecting that the measured strain has dropped below the predetermined strain threshold for greater than a first predetermined period of time.

The medical dressing may further comprise an inertial measurement unit, IMU, configured to detect motion and wherein the power management unit may be further configured to, in response to the IMU detecting a first predefined motion pattern, cause the interface to enter a reduced power mode in which the offload of data is reduced.

Detecting the first predefined motion pattern may comprise detecting that the detected motion has dropped below a predetermined motion threshold.

Detecting the first predefined motion pattern may comprise detecting that the detected motion has dropped below the predetermined motion threshold for greater than a second predetermined period of time.

The interface may be configured to, in the reduced power mode, only offload data critical to the operation of the dressing.

The strain gauge may comprise a surface with circuitry composed of graphene flakes arranged thereon.

The interface may be configured to offload data via one or more of: a wired connection and wirelessly using a wireless communication protocol.

There is also provided a medical dressing comprising: a strain gauge configured to determine the strain applied in a first direction to the dressing; a first and a second inertial measurement unit, IMUs, the first and second IMUs arranged at opposing ends of the dressing; and a controller configured to strain data from the strain gauge and receive motion data from the IMUs and to calculate the position of the first and second ends of the dressing and to adjust one or more of the calculated positions in dependence on the received strain data.

The controller may further be configured to down-weight or disregard motion data from the IMUs in dependence on the received strain data.

The controller may further be configured to down-weight or disregard motion data from the IMUs if the strain data deviates from a predetermined expected value my more than 1%, 5%, or 10%.

The predetermined expected value may be calculated based on an expected relationship between the relative positions of the IMUs and the received strain data.

The medical dressing may further comprise an interface configured to allow the medical dressing to detachably connect to an external system.

The interface may further be configured to enable the exchange of data between the controller and the external system.

The interface may further be configured to enable the exchange of data between the controller and the external system via one or more of: a universal serial bus connection, an ethernet connection, a flat flex cable connection.

DESCRIPTION OF THE DRAWINGS

The present invention will now be described by way of example with reference to the accompanying drawings. In the drawings.

DETAILED DESCRIPTION

The following description is presented to enable any person skilled in the art to make and use the invention and is provided in the context of a particular application. Various modifications to the disclosed embodiments will be readily apparent to those skilled in the art.

The general principles defined herein may be applied to other embodiments and applications without departing from the spirit and scope of the present invention. Thus, the present invention is not intended to be limited to the embodiments shown but is to be accorded the widest scope consistent with the principles and features disclosed herein.

Figure 1:
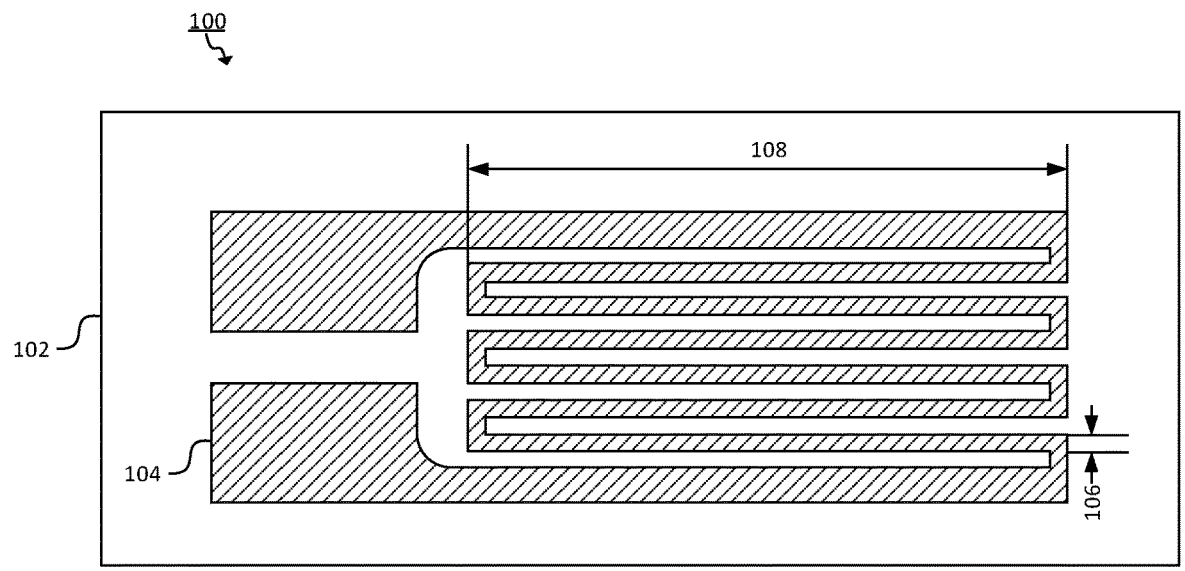
FIG. 1 shows an exemplary apparatus for measuring strain.

FIG. 1 shows an exemplary apparatus 100 that may be used to determine the force, pressure, tension or compression applied to (or equivalently, received by) an object 102 using a strain gauge 104. The strain gauge is coupled to the object. As a result, the strain gauge responds to deformation of the object as a change in electrical resistance that can then be measured. Stress can be defined as load applied to an object, and strain can be defined as the displacement and deformation that occurs as a result of an applied load. In the apparatus 100, an object 102 has a strain gauge 104 arranged thereon. Strain gauge 104 is represented by the shaded area in FIG. 1. Strain gauge 104 may fixed to the object 102 such that deformation of the object causes deformation of the strain gauge 104. The strain gauge 104 may be separated from the object 102 by an insulating material. Strain gauge 104 may comprise an electrically conducting material that forms a conducting path. The conducting path may be arranged in a pattern such that the resistance of the path increases or decreases when the strain gauge 104 is under tension or compression. The conducting path may comprise a zig-zag pattern. The conducting path of strain gauge 104 shown in FIG. 1 is arranged to be sensitive to horizontal (i.e. left to right or right to left) tension and compression and to be insensitive to vertical (i.e. up and down) tension and compression. One or more strain gauges may be wired in a Wheatstone bridge arrangement in a quarter-bridge, half-bridge, or full-bridge configuration, as is known in the art. This can assist in measuring the resistance of the strain gauge.

Figure 2:
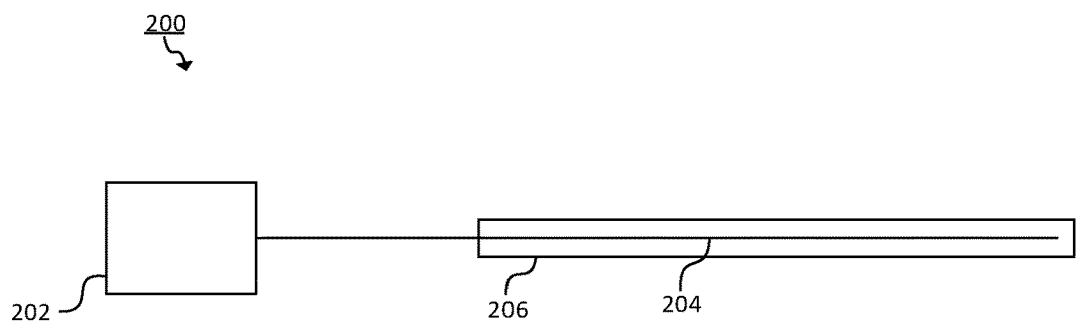
FIG. 2 shows an exemplary apparatus measuring strain in a dressing.

FIG. 2 shows an exemplary apparatus arrangement 200 for measuring strain. A controller 202 may be configured to receive signals from a strain gauge 204. Controller 202 may be connected to strain gauge 204 via a wired connection, examples of which include ethernet, universal serial bus (USB), or flat flex cable (FFC) connection.

Additionally or alternatively, controller 202 may be wirelessly connected to strain gauge 204 via one or more wireless communication protocols, including Wi-Fi®, Bluetooth® and NFC. The signals may comprise strain data or a substantially unprocessed electrical signal. In other words, the change in the resistance of the strain gauge 204 may be determined locally, at the strain gauge 204 or at the controller 202. As will be discussed later, the change in resistance may also be determined by an external host system. Where strain data is referred to herein, it may refer to a measure of strain or to a value indicative of strain and/or readily converted into a measure of strain, such as a resistance or a change in resistance. The phrase strain data does not imply the existence of strain and may be used to determine a lack of strain.

Strain gauge 204 may be attached to a medical dressing 206. It may be arranged on an external surface of the medical dressing (which may be a surface intended to be applied to a patient or a surface intended to face away from a patient) or embedded within the dressing: for example sandwiched between two structural layers of the dressing. Examples of medical dressings include wound dressings, medical strapping, adhesive dressing tape, elastic and inelastic strappings, wound pads, and bandages. Where such dressings are intended to be applied to a wound, they generally comprise a (preferably sterile) material, examples of which include gauze lint, hydrogel, porous film, an adhesive bandage (plasters) and cotton wool. As shown in FIG. 2, strain gauge 204 may be arranged within a medical dressing 206. For example, strain gauge 204 may be arranged between two layers of the dressing 206. By providing the circuitry within the dressing 206, contact between the circuitry and a human or animal body is reduced or eliminated. The arrangement shown in FIG. 2 allows the strain gauge 204 to determine the strain/force applied to dressing 206.

Figure 3:
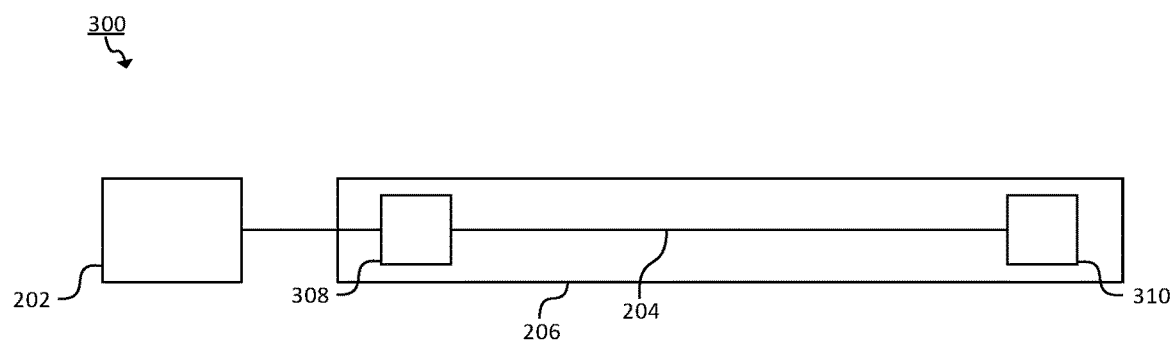
FIG. 3 shows an exemplary apparatus measuring strain in a dressing including inertial measurement units.

FIG. 3 shows an exemplary arrangement of a measurement apparatus 300. Apparatus 300 comprises the components of apparatus 200 as discussed above and further comprises a first inertial measurement unit (IMU) 308. The IMUs discussed herein may comprises one or more of: an accelerometer, a gyroscope, and a magnetometer. The IMUs may comprises multiple accelerometers, gyroscopes and magnetometers. The IMUs may comprises one accelerometer, gyroscope, and magnetometer per measurement axis. There may be three substantially orthogonal measurement axes, which may be referred to as the x, y, and z axes or alternatively as the pitch, roll, and yaw axes. The output from an IMU will be referred to as motion data. Corresponding to the instruments that the IMU comprises and depending on the processing performed the IMU, the motion data may comprise one or more of: acceleration, velocity, position, angular acceleration, angular velocity, orientation, relative change of a magnetic field, strength of a magnetic field, direction of a magnetic field. The phrase motion data does not imply the existence of motion and may be used to determine a lack of motion.

Apparatus 300 may further comprise a second IMU 310. The second IMU 310 may be separated from the first IMU 308. Preferably, the first and second IMUs 308, 310 are arranged at opposing ends of dressing 206. This arrangement allows a user to determine the position of each end of the dressing 206 in space. Arranging the IMUs at opposing ends of the dressing is advantageous as it allows the positions of the extremities of the dressing to be directly determined from which the position of the remainder of the dressing can be inferred by controller 202.

One or more of the motion data, strain data, and data indicating the position of the dressing may be subject to further processing by the controller 202 or by an external host system. Such further processing may comprise one or more of determining time averages, reducing/cancelling noise, identifying events, and calculating flexion and/or extension.

Motion data from the IMUs 308, 310 may be combined with strain data from the strain gauge 204. The position of the dressing 206, as determined from the motion data, may be adjusted in dependence on the strain data. The strain data may be adjusted in dependence on the motion data. The position of the dressing 206, as determined from the motion data, may be down-weighted or disregarded for future calculations in dependence on the strain data. Down-weighting or disregarding less useful or unwanted data can improve the quality (e.g. signal to noise ratio) and reliability of the remaining data and future calculations.

The relationship between the bending angle of a surface of an object (or similar parameters such as the curvature or radius of curvature) and the strain at that surface can be calculated theoretically. A useful approximation is obtained by approximating the object as a simple beam, i.e. is that the strain is proportional to curvature of the object or, equivalently, inversely proportional to the radius of curvature. The relationship between the bending angle of a surface of an object (or similar parameters) and the strain at that surface may also be determined empirically or experimentally.

If the strain data deviates from the expected relationship (as discussed above) by more than a predetermined amount, then the position data of the IMUs may be discarded. For example, if the strain data deviates by more than 1%, 5%, 10%, 15%, 20%, 30%, 40%, 50%, 75% or 100% from an expected value, the position data of the IMUs may be discarded. The position data of the IMUs may be down-weighted in dependence to the deviation of the strain data from its expected value. The position data of the IMUs may be down-weighted proportional to the deviation of the strain data from its expected value. Strain data may be used to adjust (according to the methods here discussed) motion data from the most proximal IMU, or the most proximal group of 2, 3 or 4 IMUs.

For example, if the motion data from the second IMU 310 indicated that it is offset by 90 degrees from the first IMU 308, but the strain data from the strain gauge 204 indicates negligible strain, this may be indicative of a malfunction in one or both of IMUs 308, 310. This may also be indicative of a malfunction in strain gauge 204 but this is less likely due to the simple nature of the strain gauge 204 and its associated circuitry when compared to a standard IMU. As with strain gauge 204, 204, one or both of IMUs 308, 310 may be arranged on the surface of a dressing 206 or arranged within the dressing 206.

The calculations discussed above could equally be applied, mutatis mutandis, to adjusting (e.g. down-weighting or disregarding) strain data based on motion data from the IMUs.

Figure 4:
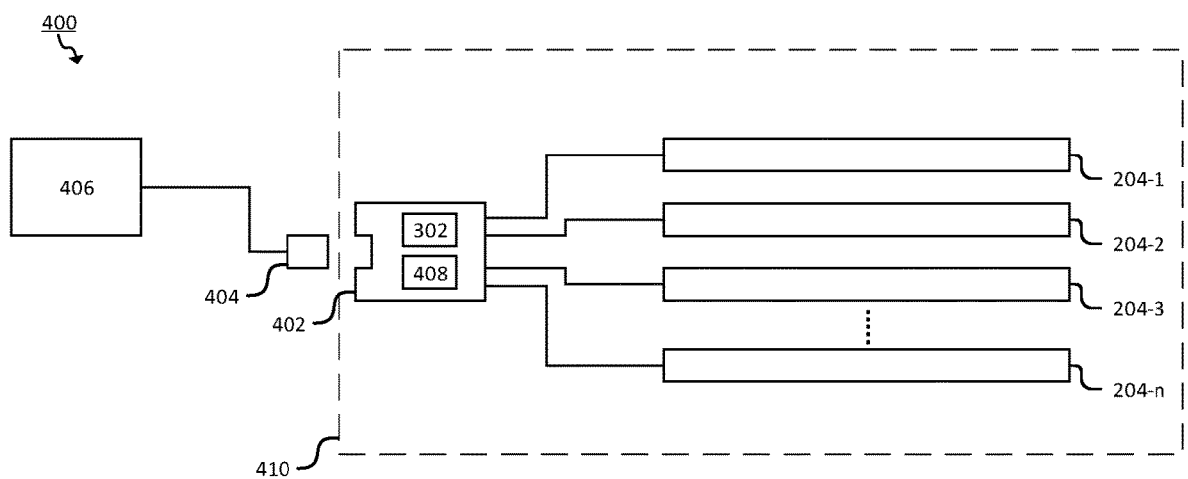
FIG. 4 shows an exemplary detachable apparatus measuring strain using multiple strain gauges.

FIG. 4 shows an exemplary apparatus 400 of the type described above with reference to FIGS. 2 and 3, further comprising an interface. The interface 402 is configured to enable data to be offloaded to an external system 406. Interface 402 may offload data via an ethernet, USB, or FFC connection. Additionally or alternatively, interface 402 may offload data via a wireless connection to the external system 406, where the wireless connection may be one or more wireless communication protocols, including Wi-Fi®, Bluetooth® and NFC.

The interface 402 may be able to enter a reduced power mode. The power mode may be controlled by a power management unit (PMU) 408. In the reduced power mode, amount of data that is offloaded may be reduced. For example, only data that is deemed critical for the operation of the apparatus may be offloaded by the interface 402 in the reduced power mode. Critical data may be the data required for continued operation of the apparatus 400. Critical data may include periodic updates indicating the status of the apparatus (for example remaining power), or strain data from a subset of measurement devices (one or more of the strain gauges 204-1 to 204-n and IMUs).

Additionally or alternatively, in the reduced power mode, the data may be offloaded less frequently than during normal operation. The frequency of data offload may be reduced in dependence on the remaining battery life. The throughput of offloaded data may be reduced in dependence on the remaining battery life. In the reduced power mode, the interface 402 may prohibit or prevent the offload of all data. If offload of data is prohibited or prevented, the measured data (strain and/or motion data) may be logged locally to be offloaded in the future. A reduced power mode is advantageous as it can extend the battery like of the apparatus 400. The apparatus 400 may comprise a power supply, examples of which include one or more batteries, solar panels, an inductive or capacitive coupling and piezo electric generators. The power supply of a device will be limited and changing batteries or providing a wired power supply to a device, particularly when said device is within a medical dressing, is inconvenient.

The power mode may be influenced by data from the measurement devices. For example, the PMU 408 may be configured to cause the interface to enter or exit the reduced power mode in response to one or more of the strain gauge(s) and the IMU(s) detecting a predefined pattern. For example, if a continuous period of low strain and/or motion is detected, the PMU 408 may cause the interface 402 to enter the reduced power mode. If a period of high strain and/or motion is detected, the PMU 408 may cause the interface 402 to exit the reduced power mode. Low/high strain and/or motion may be defined relative to long term averages. For example, if the strain and/or motion drops below a predetermined threshold, the reduced power mode may be utilised. Conversely, if the strain and/or motion rises above a predetermined threshold, the reduced power mode may be exited. The predetermine thresholds may be the long-term average, or may be within 5%, 10%, 15%, 20%, 30%, 40%, or 50% of the long-term average.

Optionally, a change in power mode may only be permitted when the strain and/or motion reading has passed the predetermined threshold for a predetermined period of time. The predetermined period of time may be selectable depending on the level of activity that is of interest to a user and whether the user desires the apparatus to react to shorter- or longer-term changes in activity. The predetermined period of time may be on the order of 1 second, 10 seconds, 1 minute, 10 minutes or 1 hour.

The aforementioned power management scheme can reduce the power consumption of the device and thus extend the useful lifetime of a battery powered device The apparatus 400 may further comprise a plurality of strain gauges 204-1 to 204-n operating in parallel. Each strain gauge 204-1 to 204-n may be configured to provide its output to a controller, as described above. The controller may be configured to provide its output to the interface 402. Alternatively, the strain gauges 204-1 to 204-n may provide their output directly to the interface 402. In some examples, the strain gauges 204-1 to 204-*n* may be stacked. In other words each strain gauge may be arranged in substantially the same orientation but displaced relative to the other gauges in or out of the plane of the strain gauge. In other words, the strain gauges may be stacked such that the gauges are arranged at increasing distances from the human or animal body. Such a stacked arrangement can be useful for determining the response of a medical dressing at various depths. For example, the force experience by each layer of a medical dressing comprising multiple layers might be determined.

In examples where parts of the apparatus are arranged on or in a medical dressing, it can be advantageous if part of the apparatus is detachable from the remainder of the apparatus. In this manner, less expensive and easily manufactured items can be located in/on the dressing which will generally be disposed after use, whilst complex processing hardware can be reused. Such an example is shown in FIG. 4. Detachable portion 410 may comprise one or more of the dressing 206, strain gauges 204, IMUs, controller 302, power management unit 408, and interface 402. Preferably, the detachable portion 410 will comprise only the strain gauges 204 and dressing 206. Detachable portion 410 may be physically detachable from the host system 406 via interface 402. Host system 406 may comprise a connector configured to engage with interface 402.

Flexion generally refers to a movement that decreases the angle between two body parts. Flexion at the elbow is decreasing the angle between the ulna and the humerus. When the knee flexes, the ankle moves closer to the buttock, and the angle between the femur and tibia gets smaller. Extension refers to a movement that increases the angle between two body parts. Extension at the elbow is increasing the angle between the ulna and the humerus. Extension of the knee straightens the lower limb. Though flexion will primarily be referred to herein, it should be appreciated that methods and apparatus described in relation to flexion may also be used to measure extension. For example, an increase in a measure of flexion will generally be accompanied by a commensurate decrease in a measure of extension from the same measurement apparatus.

Figure 5:
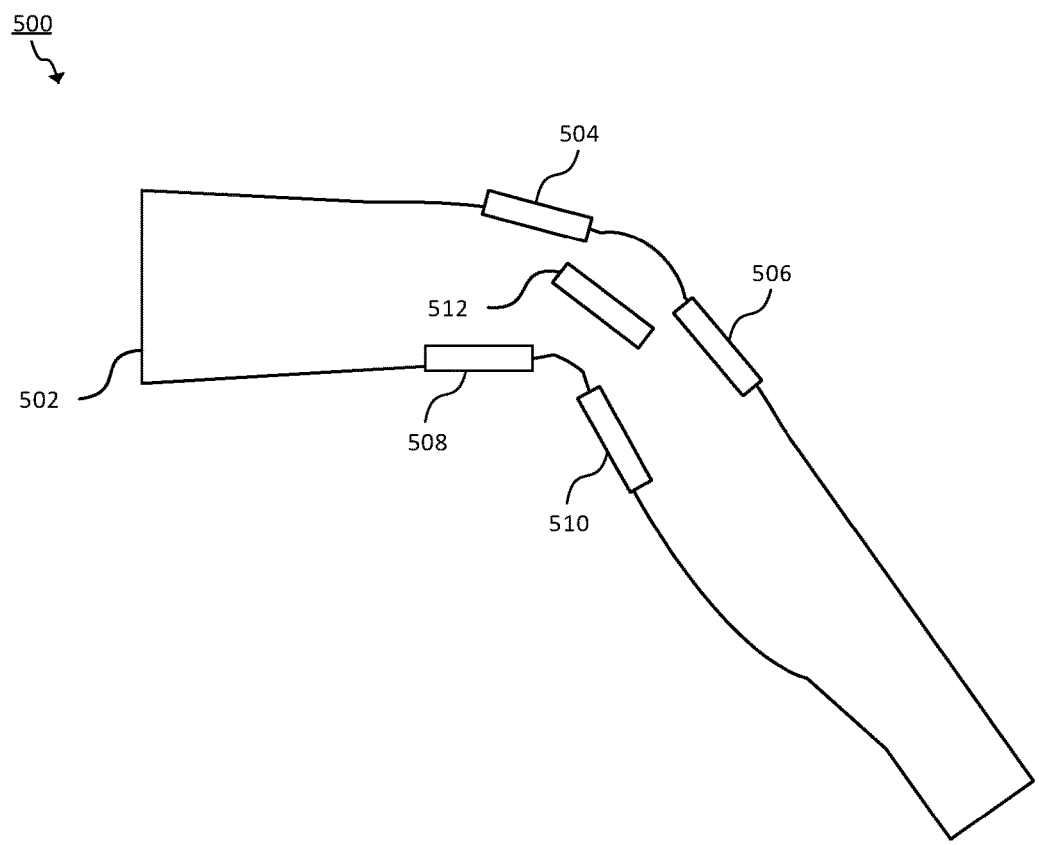
FIG. 5 shows an exemplary arrangement of strain gauges around the human knee.

FIG. 5 shows an arrangement 500 of multiple strain gauges 504-512 applied to a body 502. In this example, the strain gauges 504-512 are arranged about a human knee joint. Applying a plurality of strain gauges to a joint in a known configuration can allow the flexion of that joint to be determined from the measured strain data. The known configuration refers to a known spatial configuration. For example, if the strain data received from strain gauges 504 and 506 (arranged on the front of the leg, above and below the kneecap) increases, flexion of the knee joint can be inferred. Similarly, if the strain data received from strain gauges 504 and 506 decreases, extension of the knee joint can be inferred. The amount of flexion/extension may be assumed to be proportional to the received strain data. The plurality of strain gauges may be wired in a Wheatstone Bridge arrangement such that the effects of temperature on the gauges is cancelled.

When other configurations are used, the data from different strain gauges may be used differently. For example, if strain gauges 504 and 508 are used (respectively on the front and rear or the leg), then an increase in strain at gauge 504 and a decrease in strain at gauge 508 is indicative of flexion. From these examples, other arrangements of strain gauges and how these may be used to determine flexion and extension are apparent.

The apparatus may further comprise a manipulation unit configured to apply a force to the human or animal body. The manipulation unit may be configured to apply a force by mechanical means using, for example, motors and/or actuators. Additionally or alternatively, the manipulation unit may be configured to apply a force using piezoelectric elements or a material with a rigidity that changes with applied current (for example, by way of Joule heating) or with the application of a chemical or ionizing radiation to cause chain scission in a polymer. The manipulation unit can advantageously apply forces to the body in order to massage or limit the range of movement.

The presence of magnetic fields has been shown to affect the flow of blood in the body. The apparatus may comprise dedicated circuitry configured to produce a predefined magnetic field in order to induce changes in blood flow. The magnetic field may be pulsed in a predefined pattern in order to induce desired changes in blood flow.

The circuitry (e.g. the strain gauge, controller, interface, PMU) may be implemented in one or more application-specific integrated circuit (ASIC), a programmable logic array, a field-programmable gate array (FPGA). The circuitry may be graphene circuitry comprising a single graphene sheet, multiple individual sheets, or smaller graphene elements (such as nanoflakes) deposited on a substrate. This deposition may be done onto a wide variety of substrates including fabrics, plastics and resins. The deposited substance should preferably be immediately dried and then sandwiched between insulating layers.

Printed electronics are advantageously used on the disposable parts of the apparatus, e.g. the dressing 206. The circuitry, for example the strain gauge(s), the interface, the controller, the IMUs and/or the links therebetween may be printed in solder, tin, copper, gold, silver, nickel or a graphene-based ink (such as graphene dispersed in water with a sodium deoxycholate surfactant and a cellulose binder). An example of printed circuitry comprises metallic traces bonded to a dielectric layer (for example polyimide). An adhesive may be used to bond the conductive material to a substrate, but other types of bonding such as vapor deposition may be used. The circuitry may be printed on a printed circuit board (PCB). Certain components, e.g. the strain gauges, are particularly suited to being printed using graphene-based ink. Printing the components of the detachable portion 410 in graphene-based ink allows for simple and cheap mass production of the disposable dressing. Processing components such as the controller 302 and host system 406 may be implemented using conventional processing devices. Insulating parts of the circuitry may be also be printed. Such printed insulating parts may be printed in, for example, a boron nitride based ink. The strain gauges may comprise conducting fibres or insulating fibres doped/impregnated with a conducting material (e.g. copper, gold, silver, nickel or graphene). Examples of insulating fibres include cellulose (e.g. cotton), cellulose derivatives (e.g. sodium carbomethylcellulose), silk, wool, polyester, acrylic and nylon. Such fibres may be woven into the dressing. This can allow the strain gauge and associated electronics to be an integral part of the dressing, preventing accidental removal and improper attachment. Any exposed circuitry may be sealed by, for example, lamination. Predetermined lamination patterns may be used to allow exudate to pass through openings in said patterns.

The controller 302 and host system 406 may be any kind of device, processor, machine or dedicated circuit, or collection or portion thereof, with processing capability such that it can execute instructions. A processor may be any kind of general purpose or dedicated processor, such as a CPU, GPU, System-on-chip, state machine, media processor, an application-specific integrated circuit, a programmable logic array, a field-programmable gate array (FPGA), or the like. A computer or computer system may comprise one or more processors.

Thus, in one exemplary arrangement there is a medical dressing which comprises one or more strain gauges and optionally one or more IMUs. The dressing may be a dressing that is intended to be applied to a wound. Such a dressing may have a wound pad, e.g. of absorbent material. Alternatively, the dressing may be another form of dressing: for example a dressing intended to provide support to a body part or to hold a wound dressing in place. Such a dressing may be elastic or inelastic. It may be in the form of a tape or sheet. It may be adhesive or non-adhesive. In one convenient example it may be an adhesive tape. In another example it may be an elastic tape. The dressing comprises one or more strain gauges. The or each strain gauge may be on an external surface of the dressing or embedded within the dressing: for example sandwiched between two layers of the dressing. The strain gauge may be attached to a structural layer of the dressing so that when the dressing is deformed in at least one direction the strain gauge will sense that. Conveniently, when the strain gauge senses deformation (e.g. stretching of its bulk) it responds by a change in its electrical resistance. Where there are multiple strain gauges on the dressing, they may be arranged to sense strain in the same direction (e.g. along a longitudinal axis of the dressing) or in different directions to each other. The latter configuration can permit information to be gathered about deformation of the dressing in multiple dimensions.

The or each strain gauge may comprise a strip of graphene whose resistance changes as the gauge is exposed to strain. To that end, the graphene strip may be arranged in a zig-zag pattern or overlain slidably on another conductive or resistive element. This can be especially advantageous if the dressing comprises a therapeutic graphene region, for example a biocidal graphene region, because the two graphene regions may conveniently be deposited in a common deposition process.

A monitoring unit may be configured to receive data from the or each strain gauge and the or each IMU. It may be configured to process data received from the sensor(s) to output information relating to the therapeutic efficacy of the medical dressing. Some examples of how that may be done are:

1. The monitoring unit may respond to a detected level of strain or motion greater than a predetermined threshold by generating an alert. Such strain may be indicative of a risk that a wound protected by the dressing may be disrupted, e.g. by being re-opened.

2. The monitoring unit may respond to a maximum detected level of strain or motion in one period of time being less (e.g. by greater than a predetermined threshold) than the maximum detected level of strain or motion in an earlier period of time. Each period of time may be longer than, e.g. 1 hour. Such a reduction in strain may be indicative of a reduction in mobility which may benefit from intervention.

3. The monitoring unit may process the strain or motion of the dressing when the wearer of the dressing is undergoing therapy, e.g. physiotherapy. The monitoring unit may provide a real-time output of the level of strain or motion. This may allow a healthcare professional to observe the level of motion of a part of the wearer's body without the need for additional measuring equipment.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A method for determining a flexion or extension of a joint of a human or animal subject, comprising:
    applying a medical dressing including a plurality of strain gauges to the joint in a known configuration;
    applying a first inertial measurement unit, IMU, to each strain gauge;
    receiving strain data from each of the strain gauges;
    receiving motion data from each of the IMUs;
    and calculating the flexion or extension of the joint based on the received strain data, the received motion data, and the known configuration of the strain gauges;
    wherein the motion data received from the IMUs is adjusted by disregarding or down-weighting in the calculation of the flexion or extension based on the strain data received from the strain gauges.

2. The method of claim 1, further comprising applying a second IMU to each strain gauge, each of the first IMUs and the second IMUs being applied to opposing ends of respective strain gauges.

3. The method of claim 1, wherein the strain data is adjusted based on the motion data received from each of the IMUs.

4. The method of claim 3, wherein the strain data is disregarded or down-weighted in the calculation of the flexion or extension based on the motion data received from each of the IMUs.

5. The method of claim 1, wherein the known configuration comprises a stacked configuration.

6. The method of claim 1, wherein the plurality of strain gauges of the known configuration comprises two strain gauges being arranged on opposing sides of the joint.

7. The method of claim 1, further comprising, if the strain data from one or more of the strain gauges is greater than a predetermined threshold value, generating an alert.

8. The method of claim 1, further comprising, if the motion data from one or more of the IMUs is greater than a predetermined threshold value, generating an alert.

9. A medical dressing comprising:
    a strain gauge configured to determine a strain applied in a first direction to the dressing;
    a first and a second inertial measurement unit, IMUs, the first and second IMUs arranged at opposing ends of the dressing;
    and a controller configured to receive strain data from the strain gauge, receive motion data from the IMUs, calculate a position of a first end of the dressing and a position of a second end of the dressing based on the received motion data, and adjust one or more of the calculated positions based on the received strain data;
    wherein the controller is configured to down-weight or disregard motion data from the IMUs based on the received strain data.

10. The medical dressing as claimed in claim 9, wherein the controller is further configured to down-weight or disregard motion data from the IMUs if the strain data deviates from a predetermined expected value by more than 1%, 5%, or 10%.

11. The medical dressing as claimed in claim 10, wherein the predetermined expected value is calculated based on an expected relationship between relative positions of the IMUs and the received motion data.

12. The medical dressing as claimed claim 9, further comprising an interface configured to allow the medical dressing to detachably connect to an external system.

13. The medical dressing as claimed in claim 12, where in the interface is further configured to enable an exchange of data between the controller and the external system.

14. The medical dressing as claimed in claim 13, wherein the interface is further configured to enable the exchange of data between the controller and the external system via one or more of:
    a universal serial bus connection, an ethernet connection, a flat flex cable connection.

15. The medical dressing as claimed in claim 13, further comprising a power management unit configured to, in response to the strain gauge detecting a first predefined strain pattern, cause the interface to enter a reduced power mode in which the exchange of data is reduced.

16. The medical dressing as claimed in claim 9, wherein the strain gauge is arranged on a portion of the dressing that is detachable from a remainder of the dressing.

17. The medical dressing as claimed in claim 9, wherein one or more of the IMUs are arranged on a portion of the dressing that is detachable from a remainder of the dressing.

* * * * *